(12) United States Patent
Lin

(10) Patent No.: US 11,467,093 B2
(45) Date of Patent: Oct. 11, 2022

(54) ELECTRICAL POLARITY ADJUSTABLE BIOSENSOR BASED ON LOSSY MODE RESONANCE, BIOSENSING SYSTEM, AND METHOD OF USING THE SAME

(71) Applicant: MING CHUAN UNIVERSITY, Taipei (TW)

(72) Inventor: Yu-Cheng Lin, Taipei (TW)

(73) Assignee: MING CHUAN UNIVERSITY, Taipei (TW)

( * ) Notice: Subject to any disclaimer, the term of this patent is extended or adjusted under 35 U.S.C. 154(b) by 585 days.

(21) Appl. No.: 16/662,462

(22) Filed: Oct. 24, 2019

(65) Prior Publication Data
US 2021/0123866 A1 Apr. 29, 2021

(51) Int. Cl.
| | | |
|---|---|---|
| G01N 21/25 | (2006.01) | |
| G02B 6/26 | (2006.01) | |
| G01N 21/77 | (2006.01) | |
| C12Q 1/6825 | (2018.01) | |
| G01N 33/72 | (2006.01) | |

(52) U.S. Cl.
CPC ....... G01N 21/7703 (2013.01); C12Q 1/6825 (2013.01); G01N 21/255 (2013.01); G01N 21/7746 (2013.01); G02B 6/26 (2013.01); G01N 33/723 (2013.01)

(58) Field of Classification Search
None
See application file for complete search history.

(56) References Cited

U.S. PATENT DOCUMENTS

| | | | | |
|---|---|---|---|---|
| 2002/0140937 A1* | 10/2002 | Lieberman | ........... | G01N 21/553 356/445 |
| 2008/0266568 A1* | 10/2008 | VanWiggeren | ...... | G01N 21/553 356/445 |
| 2009/0109441 A1* | 4/2009 | Hartman | ............ | G01N 21/1717 356/477 |
| 2010/0267165 A1* | 10/2010 | Bruls | ................. | G01N 21/1717 422/69 |
| 2011/0001975 A1* | 1/2011 | Razansky | ................. | G01J 5/08 356/445 |

FOREIGN PATENT DOCUMENTS

JP 2003279479 A * 10/2003 ......... A61B 5/14525

OTHER PUBLICATIONS

Del Villar, Ignacio, et al. "Design rules for lossy mode resonance based sensors." Applied optics 51.19 (2012): 4298-4307. (Year: 2012).*

* cited by examiner

Primary Examiner — Shawn Decenzo
(74) Attorney, Agent, or Firm — Chun-Ming Shih; HDLS IPR Services

(57) ABSTRACT

An electrical polarity adjustable biosensor based on lossy mode resonance includes a first polarity module, a second polarity module, and a plurality of spacers disposed between the first polarity module and the second polarity module. A biomaterial sensing region for injecting an object to be tested is formed between a bioprobe layer of the first polarity module and a second electrode layer of the second polarity module. An electric field is formed between a lossy mode resonance layer of the first polarity module and the second electrode layer, and the electric field acts on a plurality of bioprobes of the bioprobe layer and the object to be tested. The present disclosure further includes a method of using the electrical polarity adjustable biosensor based on lossy mode resonance.

10 Claims, 5 Drawing Sheets

ELECTRICAL POLARITY ADJUSTABLE BIOSENSOR BASED ON LOSSY MODE RESONANCE, BIOSENSING SYSTEM, AND METHOD OF USING THE SAME

BACKGROUND

Technical Field

The present disclosure relates to a biosensor, a biosensing system, and a method of using the same, and more particularly to a biosensor, a biosensing system with an electrical polarity adjustable function, and a method of using the same is based on the principle of lossy mode resonance (LMR).

Description of Related Art

The statements in this section merely provide background information related to the present disclosure and do not necessarily constitute prior art.

In modern life, the life style of human beings changes with the development of the country and society. In the era of rapid technological development and convenient medical services, many countries have never developed into developing stage countries or developed stage countries, enjoying the convenience brought by technology is no longer a dream. The distance between countries is no longer a distance, no matter industry, information, culture and food. But with the convenience of life and longevity, civilized diseases have also emerged, such as heart disease, cancer, obesity and diabetes. Taking diabetes as an example, the main symptom is that the patient's blood sugar is higher than the standard value for a long time. Normally, when the body's blood sugar rises, it should be controlled by insulin to lower blood sugar. In the diabetes test, glycosylated hemoglobin (HbA1c) can be tested for the basis of blood glucose status for nearly 3 months.

In the past few years of bio-detection technology, surface plasmon resonance (SPR) technology has made great progress, and its high sensitivity makes it widely used in the biological and chemical fields for molecular grade detection. In many research works, the surface plasmon resonance (SPR) sensor is constructed by using a high refractive index prism with a metal layer on the surface. The angle of an incidence light has widely adjustable range. Therefore, any medium and the object to be tested can find a suitable angle to excite the surface plasma, and the incident light undergoes total internal reflection (TIR) at the interface between an optical waveguide and a resonance film and generates an evanescent wave. An incident light comprising a transverse electronic (TE) wave and transverse magnetic (TM) waves, surface plasmon resonance (SPR) technology can only excite the TM wave. As for selection for material of the metal layer, element of the surface plasma resonance generally has a better effect on a precious metal material such as gold or silver, but has the disadvantage that the material is expensive and easily oxidized. Furthermore, the sensor architecture using the prime-type design usually has a large volume, requires expensive optical equipment (such as lens group) and precision mechanical equipment (such as optical table systems), and is not easy to achieve miniaturization and mass production.

However, many biomolecules are greatly affected by electrical polarity, the biomolecules exhibit different biological responses and behavioral patterns in different electric field environments. The SPR and the LMR in prior art cannot control the electrical polarity. For fixation or capture of polar molecules of an object to be tested, only random sampling can be used. Therefore, sampling rate of the object to be tested is low, and detection efficiency and quality cannot be improved. Therefore, how to design a biosensor to solve the technical problems above is an important subject studied by the inventors and proposed in the present disclosure.

SUMMARY

A purpose of the present disclosure is to provide an electrical polarity adjustable biosensor based on lossy mode resonance, which has characteristics with low cost, miniaturization and easy operation, and can improve a sampling rate of an object to be tested by adjusting electrical polarity, thereby achieving a purpose of improving detection efficiency and detection quality.

In order to achieve the purpose above-mentioned, the electrical polarity adjustable biosensor based on lossy mode resonance includes a first polarity module, a second polarity module and a plurality of spacers. The first polarity module includes an optical waveguide layer, a lossy mode resonance layer and a bioprobe layer stacked on each other, the lossy mode resonance layer is disposed on one side of the optical waveguide layer, and two opposite sides of the optical waveguide layer being a light input end and a light output end, the bioprobe layer has a plurality of bioprobes, one plane of the bioprobe layer is disposed on the lossy mode resonance layer. The second polarity module is disposed opposite to the first polarity module, the second polarity module includes a substrate and a second electrode layer stacked on each other, the second electrode layer adjacent to but not in contact with the bioprobe layer. The plurality of spacers is disposed between the first polarity module and the second polarity module, the plurality of spacers simultaneously contacts with the other plane of the bioprobe layer and the second electrode layer, and separate the bioprobe layer and the second electrode layer. A biomaterial sensing region is formed between the lossy mode resonance layer and the second electrode layer, and the biomaterial sensing region has the plurality of bioprobes, the plurality of bioprobes are formed by performing a surface modification on the lossy mode resonance layer, and the biomaterial sensing region is for injecting an object to be tested. An electric field is formed between the lossy mode resonance layer and the second electrode layer, the electric field acts on at least one of the pluralities of bioprobes and the object to be tested.

Further, the lossy mode resonance layer is a transparent conductive layer.

Further, the bioprobe layer is composed of a metal oxide or a polymer material.

Further, the optical waveguide layer is one of a glass substrate, a quartz substrate, a photonic crystal substrate, and a polymer material substrate.

Further, the plurality of bioprobes are composed of a boride functional group or a DNA probe.

Another purpose of the present disclosure is to provide an electrical polarity adjustable biosensing system based on lossy mode resonance includes a broadband light source, an input optical fiber, a sensing module, an output optical fiber and a spectrometer. The input optical fiber is coupled to the broadband light source. The sensing module is coupled to the input optical fiber, and the sensing module includes a first polarity module, a second polarity module and a plurality of spacers. The first polarity module includes an optical waveguide layer, a lossy mode resonance layer and a bioprobe layer stacked on each other, the lossy mode resonance layer is disposed on one side of the optical waveguide layer, and two opposite sides of the optical waveguide layer being a light input end and a light output end, the bioprobe layer has a plurality of bioprobes, one plane of the bioprobe layer is disposed on the lossy mode resonance layer. The second polarity module is disposed opposite to the first polarity module, the second polarity module includes a substrate and a second electrode layer stacked on each other, the second electrode layer adjacent to but not in contact with the bioprobe layer. The plurality of spacers is disposed between the first polarity module and the second polarity module, the plurality of spacers simultaneously contacts with the other plane of the bioprobe layer and the second electrode layer, and separate the bioprobe layer and the second electrode layer. The output optical fiber is coupled to the light output end. The spectrometer is coupled to the output optical fiber. An incident light emitted by the broadband light source is configured to lossy mode resonance in the sensing module, a biomaterial sensing region is formed between the lossy mode resonance layer and the second electrode layer, and the biomaterial sensing region has the plurality of bioprobes, the plurality of bioprobes are formed by performing a surface modification on the lossy mode resonance layer, and the biomaterial sensing region is for injecting an object to be tested. An electric field is formed between the lossy mode resonance layer and the second electrode layer, the electric field acts on at least one of the pluralities of bioprobes and the object to be tested.

Further, the electrical polarity adjustable biosensing system based on lossy mode resonance further includes an optical fiber attenuator and an analysis host is coupled to the optical fiber attenuator, the optical fiber attenuator is coupled to the input optical fiber, and the analysis host is coupled to the spectrometer.

Further, the lossy mode resonance layer is a transparent conductive layer, the plurality of bioprobes are composed of a boride functional group or a DNA probe.

More another purpose of the present disclosure is to provide a method of using an electrical polarity adjustable biosensor based on lossy mode resonance, including following steps of: Placing an object to be tested on a biomaterial sensing region having a plurality of bioprobes. Inputting an incident light emitted by a broadband light source to an optical waveguide layer is disposed under the plurality of bioprobes. Energizing a lossy mode resonance layer and a second electrode layer to generate an electric field that acts on at least one of the pluralities of bioprobes and the object to be tested. Measuring a light outputted from the optical waveguide layer by a spectrometer. The biomaterial sensing region is formed by sandwiching a plurality of spacers between the lossy mode resonance layer and the second electrode layer, and the plurality of bioprobes are formed by performing a surface modification on the lossy mode resonance layer.

Further, the plurality of bioprobes are composed of a boride functional group or a DNA probe, the lossy mode resonance layer is a transparent conductive layer, and a substrate is stacked on one plane of the second electrode layer away from the plurality of spacers. When the electrical polarity adjustable biosensor based on lossy mode resonance is used, since the biomaterial sensing region includes the bioprobe layer has been surface modified, when the plurality of bioprobes are composed of a boride functional group, the biomaterial sensing region can detect a glycated hemoglobin (HbA1c). In addition, the electrical polarity adjustable biosensor based on lossy mode resonance is quite suitable for miniaturization. The optical waveguide layer may select a glass substrate which has lower costs and smaller volume then a prism, and the bioprobe layer and the lossy mode resonance layer may be selected from a light transmissive metal oxide such as indium tin oxide (ITO), zinc oxide (ZnO) or titanium oxide ($TiO_2$) which with mature process and high yield coating technology (such as RF magnetron sputter). Further, the electric field is formed between the lossy mode resonance layer and the second electrode layer may act on the plurality of bioprobes and the object to be tested. In detection process for the object to be tested, the electrical polarity can be controlled by generating the electric field, thereby increasing sampling rate of polar molecules of the object to be tested, so that the operation of measuring the object to be tested is convenient.

Therefore, the electrical polarity adjustable biosensor based on lossy mode resonance of the present disclosure has the characteristics with low cost, miniaturization and easy operation, and can improve the sampling rate of the object to be tested by adjusting electrical polarity, thereby achieving the purpose of improving detection efficiency and detection quality. In addition, lossy mode resonance (LMR) has the following characteristics compare with surface plasma resonance (SPR): both TE wave and TM wave can resonate with the lossy mode resonance layer. However, SPR technology can only resonate with TM waves.

In order to further understand the techniques, means, and effects of the present disclosure for achieving the intended purpose. Please refer to the following detailed description and drawings of the present disclosure. The drawings are provided for reference and description only, and are not intended to limit the present disclosure.

DETAILED DESCRIPTION

Figure 1:
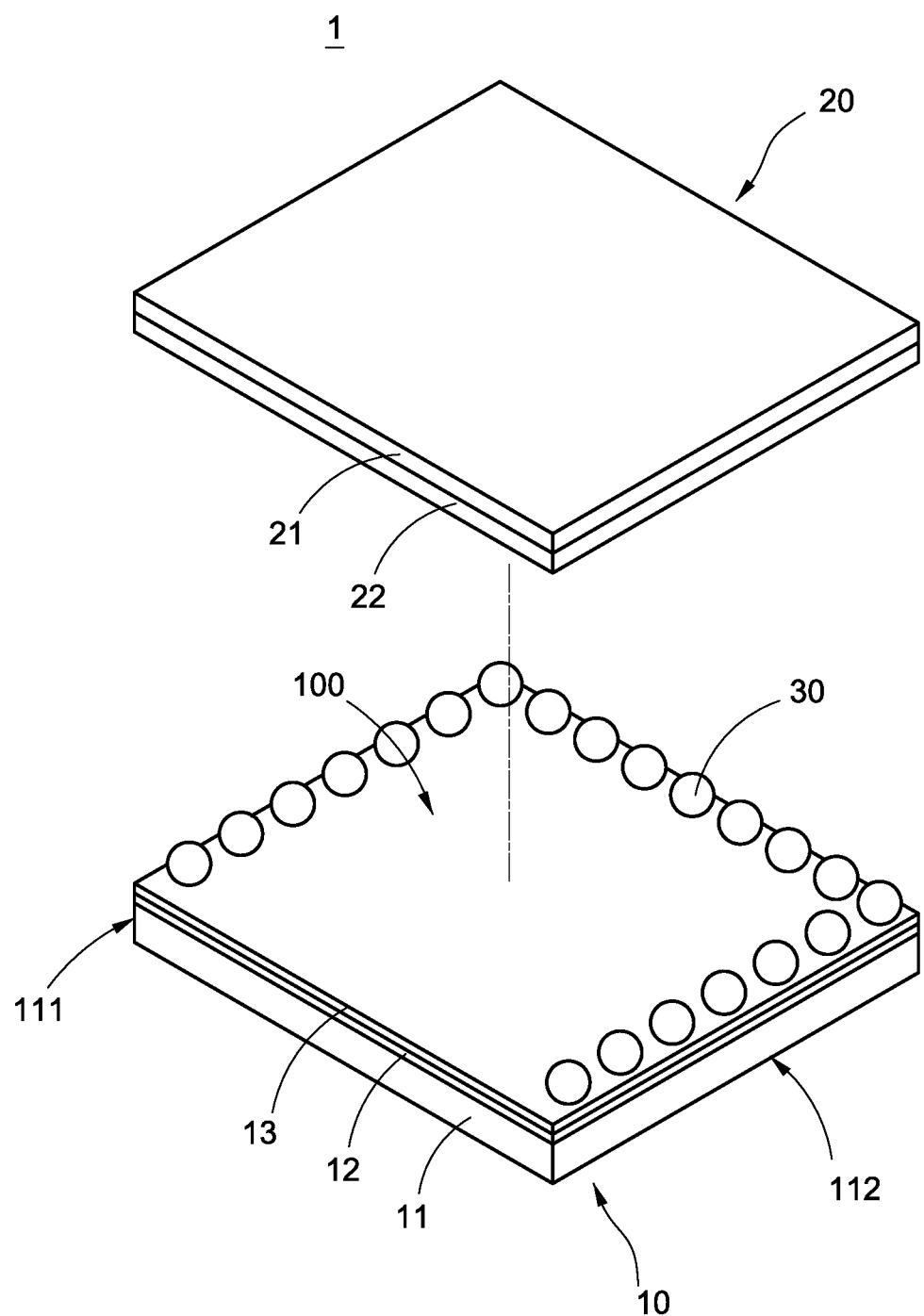
FIG. 1 is a schematic exploded diagram of an electrical polarity adjustable biosensor based on lossy mode resonance of the present disclosure.

The embodiments of the present disclosure are described by way of specific examples, and those skilled in the art can readily appreciate the other advantages and functions of the present disclosure. The present disclosure may be embodied or applied in various other specific embodiments, and various modifications and changes can be made without departing from the spirit and scope of the present disclosure.

It should be understood that the structures, the proportions, the sizes, the number of components, and the like in the drawings are only used to cope with the contents disclosed in the specification for understanding and reading by those skilled in the art, and it is not intended to limit the conditions that can be implemented in the present disclosure, and thus is not technically significant. Any modification of the structure, the change of the proportional relationship, or the adjustment of the size, should be within the scope of the technical contents disclosed by the present disclosure without affecting the effects and the achievable effects of the present disclosure.

The technical content and detailed description of the present disclosure will be described below in conjunction with the drawings.

Figure 2:
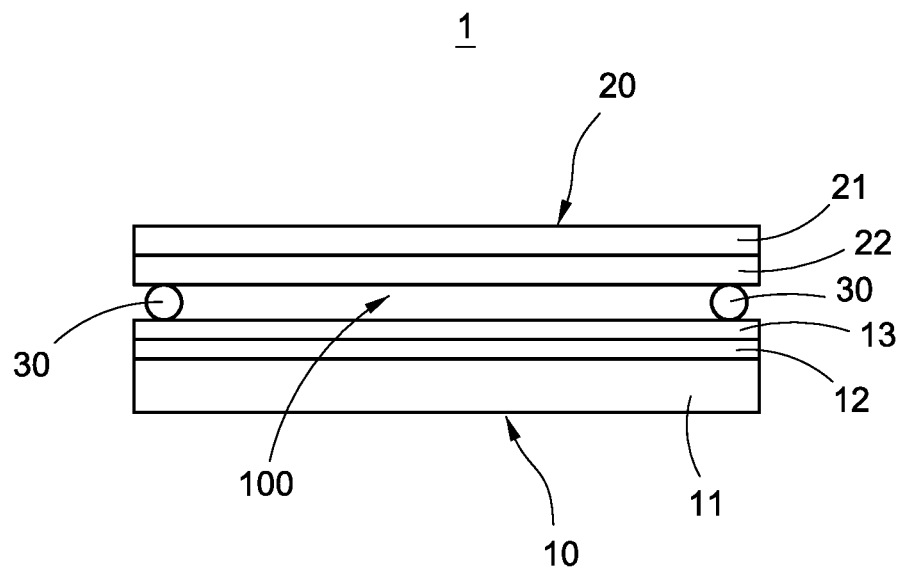
FIG. 2 is a schematic cross-sectional diagram of the electrical polarity adjustable biosensor based on lossy mode resonance of the present disclosure.

Please refer to FIG. 1 and FIG. 2. FIG. 1 is a schematic exploded diagram of an electrical polarity adjustable biosensor based on lossy mode resonance of the present disclosure. FIG. 2 is a schematic cross-sectional diagram of the electrical polarity adjustable biosensor based on lossy mode resonance of the present disclosure.

One embodiment of an electrical polarity adjustable biosensor 1 based on lossy mode resonance of the present disclosure includes a first polarity module 10, a second polarity module 20, and a plurality of spacers 30. The first polarity module 10 including an optical waveguide layer 11, a lossy mode resonance layer 12 and a bioprobe layer 13 stacked on each other. The lossy mode resonance layer 12 is disposed on one side of the optical waveguide layer 11, and two opposite sides of the optical waveguide layer 11 are a light input end 111 and a light output end 112. The bioprobe layer 13 having a plurality of bioprobes, one plane of the bioprobe layer 13 is disposed on the lossy mode resonance layer 12.

Further, the optical waveguide layer 11 may be one of a glass substrate, a quartz substrate, a photonic crystal substrate, and a polymer material substrate, or may be made of other materials having low light loss. Although the optical fiber sensor is currently in the mainstream, a manufacturing process of the optical fiber sensor needs to be ground and coated, which is not easy to manufacture. Taking a plastic optical fiber (POF) as an example, although the toughness thereof is better, it is difficult to resist the organic solution and high temperature in the process, and the wavelength range of the absorption spectrum of POF is between red light and infrared light. The absorption spectrum is a commonly used wavelength and is not easily used to determine SPR and LMR phenomena. Taking a glass optical fiber (GOF) as an example, although it can resist the organic solution and high temperature in the process, and the absorption spectrum is in ultraviolet light, and the ultraviolet light is not a commonly used wavelength, the grinding is not easy and is easy to break. In summary, the present disclosure proposes to use a planar waveguide base on glass as a sensor, and the glass substrate is first coated and then cut to an appropriate size. Glass can resist the organic solution and high temperature in the process, and does not need to be ground. Compared with the optical fiber sensor, the planar waveguide makes the sensor easier, is not easy to damage, and has high yield. The lossy mode resonance layer 12 may be composed of a metal oxide such as one of indium tin oxide (ITO), zinc oxide (ZnO), or titanium oxide ($TiO_2$) or a polymer material.

The second polarity module 20 is disposed opposite to the first polarity module 10, the second polarity module 20 includes a substrate 21 and a second electrode layer 22 stacked on each other, the second electrode layer 22 is adjacent to but not in contact with the bioprobe layer 13. The second electrode layer 22 may be composed of a metal or a metal oxide with electronic conductivity such as indium tin oxide (ITO).

The plurality of spacers 30 are disposed between the first polarity module 10 and the second polarity module 20, the plurality of spacers 30 simultaneously contact the other plane of the bioprobe layer 13 and the second electrode layer 22, and separate the bioprobe layer 13 and the second electrode layer 22. The plurality of spacers 30 may be a spacer or a PS spacer layer used in the general display field, and are electrically insulating materials. In the embodiment of the present disclosure, a plurality of spacers 30 are disposed on three or two edges of all four edges of the bioprobe layer 13, and one of edges is reserved for injecting an object to be tested (or call a device under test, DUT).

Further, a biomaterial sensing region 100 is formed between the lossy mode resonance layer 12 and the second electrode layer 22, and the biomaterial sensing region 100 has the plurality of bioprobes, the plurality of bioprobes are formed by performing a surface modification on the lossy mode resonance layer 12, and the biomaterial sensing region 100 is for injecting the object to be tested. In the embodiment of the present disclosure, the plurality of bioprobes are composed of a boride functional group or a DNA probe.

The lossy mode resonance layer 12 may be selected a metal oxide such that the real part of the dielectric constant is much larger than the imaginary part of the dielectric constant, there is an opportunity to generate a lossy mode. In the embodiment of the present disclosure, the object to be tested may be a phosphate buffer solution (PBS) including glycated hemoglobin (HbA1c). In addition, the lossy mode resonance layer 12 may also form a DNA probe after surface modification, the DNA probe is used to combine with complementary DNA.

The principle of LMR is similar to the principle of SPR. When an incident light enters the lossy mode resonance layer 12 at a critical angle and total internal reflection (TIR) occurs, the incident light generates an evanescent wave on the surface of the lossy mode resonance layer 12. When the evanescent wave is matched with the effective refractive index of the lossy mode resonance layer 12, they are coupled to observe the light intensity loss of the partial wavelength from a spectrum of reflected light. The wavelength with loss of light intensity is called an LMR wavelength and is a focus of observation in the present disclosure. In addition, both TE wave and TM wave can resonate with the lossy mode resonance layer 12, so there is no need to polarize or filter the incident light, and the sensitivity is high and the use is convenient.

In the present embodiment, the indium tin oxide layer as the lossy mode resonance layer 12 is disposed on the glass substrate as the optical waveguide layer 11 by RF magnetron sputter. RF magnetron sputter is well known and mature in the art and will not be described in detail herein. The surface modification is carried out sequentially in the following steps of: removing surface contaminants of an indium tin oxide layer, carrying out a hydroxylate treatment to the indium tin oxide layer, carrying out a silanization treatment to the indium tin oxide layer, and carrying out a decarboxylation treatment for the indium tin oxide layer.

Figure 3:
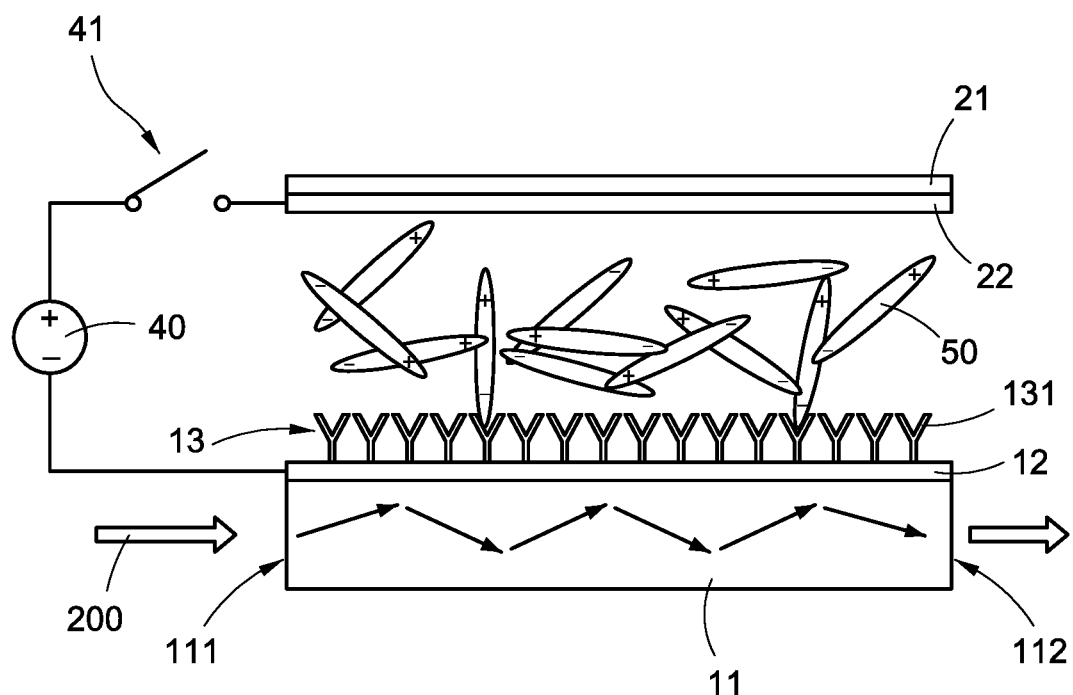
FIG. 3, 4 are schematic diagrams showing operation of the electrical polarity adjustable biosensor based on lossy mode resonance of the present disclosure.
Figure 4:
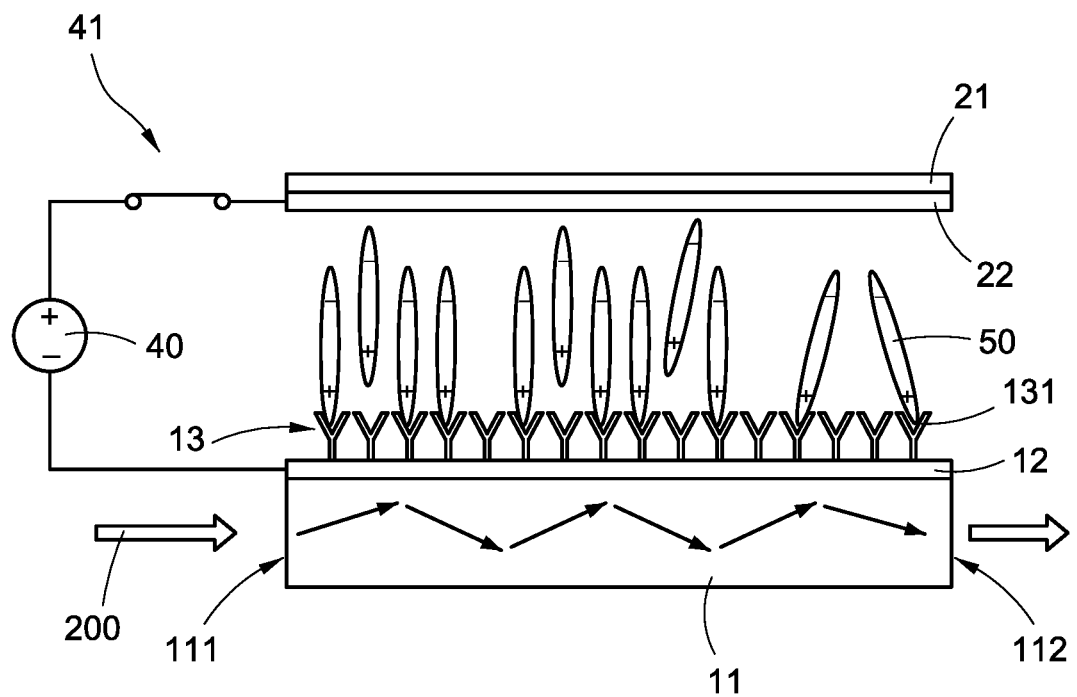

Please refer to FIG. 3 and FIG. 4. FIG. 3, 4 are schematic diagrams showing operation of the electrical polarity adjustable biosensor based on lossy mode resonance of the present disclosure. In the embodiment of the present disclosure, an electric field is formed between the lossy mode resonance layer 12 and the second electrode layer 22, the electric field acts on at least one of the pluralities of bioprobes 131 and the object to be tested. The object to be tested has polar molecules 50, the object to be tested is injected between the first polarity module 10 and the second polarity module 20, and the bioprobe layer 13 includes the plurality of bioprobes 131 (presenting a "Y" shape).

As shown in FIG. 3, when the lossy mode resonance layer 12 and the second electrode layer 22 are not electrically connected to the power source 40 (the switch 41 is an open circuit, or call OFF state), majority of polar molecules 50 are disorderly arranged. At this time, majority of the bioprobes 131 cannot be combined with the polar molecules 50 in a correct position. Therefore, for fixation or capture of the polar molecules 50 of an object to be tested, only random sampling can be used, sampling rate of the polar molecules 50 is low. A light 200 incident to the light input end 111 and output from the light output end 112 cannot be effectively resonated in the lossy mode resonance layer 12, and the detection efficiency and quality cannot be improved.

As shown in FIG. 4, when the lossy mode resonance layer 12 and the second electrode layer 22 are electrically connected to the power source 40 (the switch 41 is a short circuit, or call ON state), an electric field is formed between the lossy mode resonance layer 12 and the second electrode layer 22, and majority of the polar molecules 50 are arranged in an orderly manner according to the electric field. At this time, majority of the bioprobes 131 can be combined with the polar molecules 50 at the correct position, and the sampling rate of the polar molecules 50 is high. A light 200 incident to the light input end 111 and output from the light output end 112 can be effectively resonated in the lossy mode resonance layer 12. Therefore, the electrical polarity can be controlled by generating the electric field, thereby increasing sampling rate of polar molecules of the object to be tested, thereby achieving a purpose of improving detection efficiency and detection quality.

Figure 5:
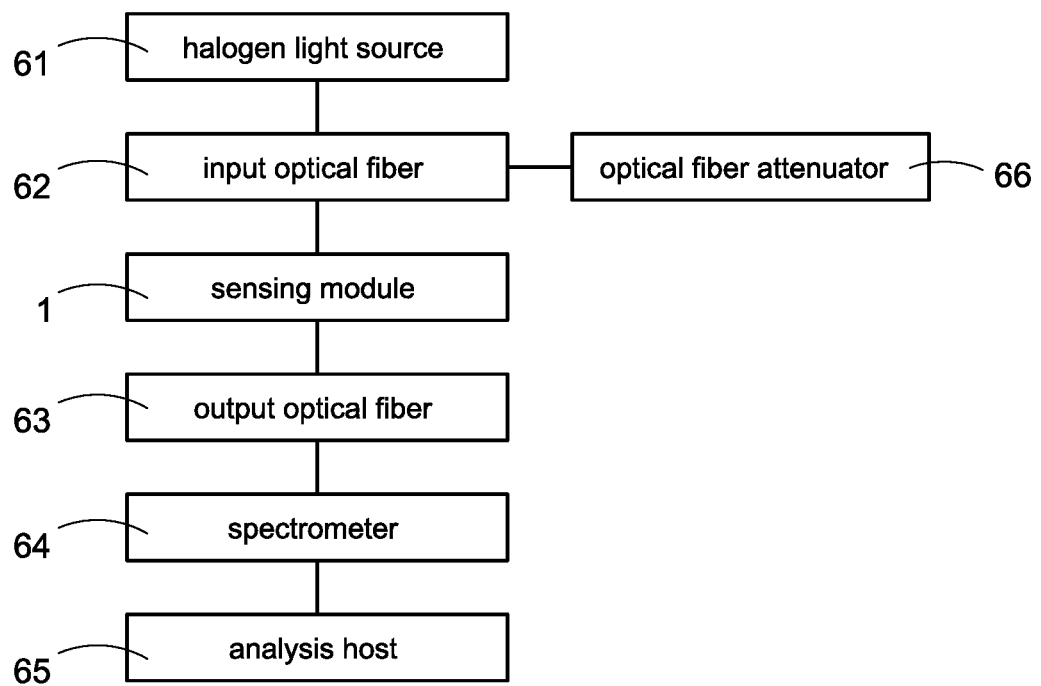
FIG. 5 is a schematic function block diagram of the electrical polarity adjustable biosensor based on lossy mode resonance of the present disclosure.
Figure 6:
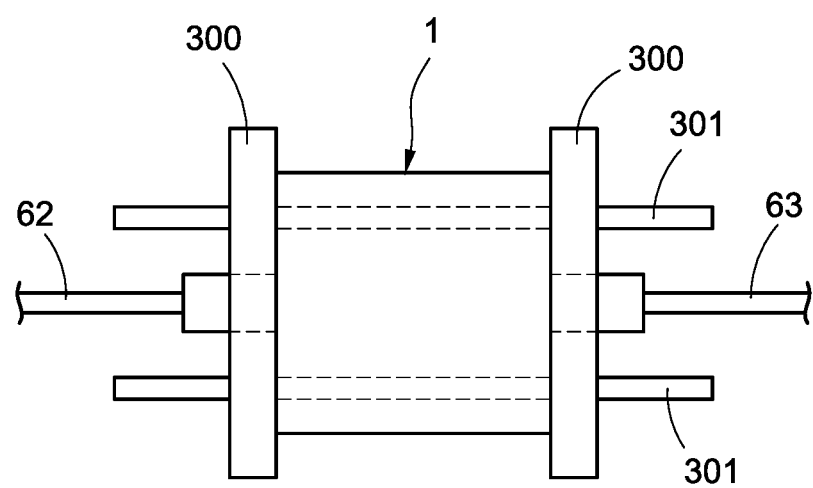
FIG. 6 is a schematic diagram of a jig for a fixed sensing module in the electrical polarity adjustable biosensor based on lossy mode resonance of the present disclosure.

Please refer to FIG. 5 and FIG. 6. FIG. 5 is a schematic function block diagram of the electrical polarity adjustable biosensor based on lossy mode resonance of the present disclosure. FIG. 6 is a schematic diagram of a jig for a fixed sensing module in the electrical polarity adjustable biosensor based on lossy mode resonance of the present disclosure.

As shown in FIG. 5, when the electrical polarity adjustable biosensor 1 based on the lossy mode resonance is disposed in a system for measurement, the electrical polarity adjustable biosensor 1 as a sensing module coupling a broadband light source (such as the halogen light source 61 shown in the figure) by coupling an input optical fiber 62. The electrical polarity adjustable biosensor 1 is coupled to a spectrometer 64 by coupling an output optical fiber 63. Finally, the spectrometer 64 can be coupled to an analysis host 65 for analysis of measured values. An optical fiber attenuator 66 can be added to the input optical fiber 62, and the amount of light intensity attenuation can be manually adjusted. In this embodiment, the halogen light source 61 used may generate incident light having a wavelength range of 400 nm to 1800 nm. The wavelength range detectable by spectrometer 64 is suitable for the halogen light source 61. When the electrical polarity adjustable biosensor 1 is used in the system, the object to be tested is placed in the biomaterial sensing region 100, an incident light emitted by the halogen light source 61 is input to glass substrate as the optical waveguide layer 11 by the light input end 111, and energizing the lossy mode resonance layer 12 and a second electrode layer 22. Finally, the light (i.e., the light reflected from the bioprobe layer 13) output from the light output end 112 of the glass substrate is measured by the spectrometer 64.

As shown in FIG. 6, during a measurement process, a jig 300 may be disposed between the input optical fiber 62 and the output optical fiber 63, and a jig 300 may be used to fix the electrical polarity adjustable biosensor 1 to build a measurement platform. In the present embodiment, the jig 300 can be made of stainless steel and matched with an adjustable slide rail 301 to match different sizes of the electrical polarity adjustable biosensor 1 to make measurement and application more convenient. The measuring platform of this embodiment is applied to the input optical fiber 62 and the output optical fiber 63 of fiber connector (FC). When a thickness of the glass substrate is 0.7 mm, the center of the two sides of the fiber corresponds to the position of the glass at 0.35 mm (at the center of the glass substrate). In this way, the incident light can be efficiently collected, and even if the thickness of the glass substrate is increased, it can be incident into the glass substrate.

The indium tin oxide layer on the glass substrate itself cannot adsorb HbA1c, and indium tin oxide (ITO) must be bonded to the boride functional group through the surface modification, so let the boride functional group adsorbs HbA1c. The LMR wavelength is also displaced when the indium tin oxide layer is adsorbed to HbA1c, thereby achieving purpose for detection. The first step is cleaning, and the indium tin oxide layer as the lossy mode resonance layer 12 is sequentially washed with acetone, absolute ethanol, ultrapure water, potassium hydroxide aqueous solution, and ultrapure water. The second step is a hydroxylation treatment, and the lossy mode resonance layer 12 is washed with an RCA solution (i.e., a mixed solution of ammonia water and hydrogen peroxide) to remove organic contaminants and generate hydroxyl groups (OH). The third step is the silanization treatment, the hydroxyl group is attached to the silane, leaving the end with isocyanate and boric acid combined. The fourth step is a decarboxylation treatment to remove the carboxyl group (COOH) to facilitate the bonding of the isocyanate group to the benzene ring, carbon dioxide is generated during the reaction, so that bubble generation can be observed. That is, the surface modification has been successful.

In research of the present disclosure, LabView and Mathscript are used to simulate LMR to cause TE wave and TM wave loss. There are four parameters in the program for the user to adjust, including: glass substrate thickness ($d_1$), ITO thickness ($d_2$), the length of the sensing area (L) and the refractive index of the object to be tested ($n_3$). There are two parameters that vary with the wavelength of the incident light, including glass substrate refractive index ($n_1$) and ITO refractive index ($n_2$). The most obvious parameter affecting LMR sensitivity is ITO thickness ($d_2$), which is one of the characteristics of LMR. SPR cannot improve the sensitivity of the sensor by the thickness of the resonance layer. According to the simulation results, in the case of L=30 mm and d1=30 mm, if the ITO thickness is thinner, the loss of LMR wavelength is increased, which is beneficial to signal extraction and sensitivity, and the transmittance is about −10 dB to −20 dB, the incident light intensity is different from the reflected light intensity by 10 to 100 times.

When the electrical polarity adjustable biosensor 1 based on lossy mode resonance is used, since the biomaterial sensing region 100 includes the bioprobe layer has been surface modified, when the plurality of bioprobes 131 are composed of a boride functional group, the biomaterial sensing region 100 can detect a glycated hemoglobin (HbA1c). In addition, the electrical polarity adjustable biosensor 1 based on lossy mode resonance is quite suitable for miniaturization. The optical waveguide layer 11 may select a glass substrate which has lower costs and smaller volume then a prism, and the bioprobe layer 13 and the lossy mode resonance layer 12 may be selected from a light transmissive metal oxide such as indium tin oxide (ITO), zinc oxide (ZnO) or titanium oxide ($TiO_2$) which with mature process and high yield coating technology (such as RF magnetron sputter). Further, the electric field is formed between the lossy mode resonance layer 12 and the second electrode layer 22 may act on the plurality of bioprobes 131 and the object to be tested. In detection process for the object to be tested, the electrical polarity can be controlled by generating the electric field, thereby increasing sampling rate of polar molecules 50 of the object to be tested, so that the operation of measuring the object to be tested is convenient.

Therefore, the electrical polarity adjustable biosensor based on lossy mode resonance of the present disclosure has the characteristics with low cost, miniaturization and easy operation, and can improve the sampling rate of the object to be tested by adjusting electrical polarity, thereby achieving the purpose of improving detection efficiency and detection quality. The applicable fields of the present disclosure may cover drug research, medical diagnosis, environmental monitoring, and food safety.

In addition, lossy mode resonance (LMR) has the following characteristics compare with surface plasma resonance (SPR): both TE wave and TM wave can resonate with the lossy mode resonance layer 12. However, SPR technology can only resonate with TM waves.

The above is only a detailed description and drawings of the preferred embodiments of the present disclosure, but the features of the present disclosure are not limited thereto, and are not intended to limit the present disclosure. All the scope of the present disclosure shall be subject to the scope of the following claims. The embodiments of the spirit of the present disclosure and its similar variations are intended to be included in the scope of the present disclosure. Any variation or modification that can be easily conceived by those skilled in the art in the field of the present disclosure can be covered by the following claims.

What is claimed is:

1. An electrical polarity adjustable biosensor based on lossy mode resonance comprising:
    a first polarity module including an optical waveguide layer, a lossy mode resonance layer and a bioprobe layer stacked on each other, the lossy mode resonance layer disposed on one side of the optical waveguide layer, and two opposite sides of the optical waveguide layer being a light input end and a light output end, the bioprobe layer having a plurality of bioprobes, one plane of the bioprobe layer disposed on the lossy mode resonance layer,
    a second polarity module disposed opposite to the first polarity module, the second polarity module including a substrate and a second electrode layer stacked on each other, the second electrode layer adjacent to but not in contact with the bioprobe layer, and
    a plurality of spacers disposed between the first polarity module and the second polarity module, the plurality of spacers simultaneously contacts with the other plane of the bioprobe layer and the second electrode layer, and separate the bioprobe layer and the second electrode layer,
    wherein, a biomaterial sensing region is formed between the lossy mode resonance layer and the second electrode layer, and the biomaterial sensing region has the plurality of bioprobes, the plurality of bioprobes are formed by performing a surface modification on the lossy mode resonance layer, and the biomaterial sensing region is for injecting an object to be tested,
    wherein, an electric field is formed between the lossy mode resonance layer and the second electrode layer, the electric field acts on at least one of the pluralities of bioprobes and the object to be tested.

2. The electrical polarity adjustable biosensor based on lossy mode resonance in claim 1, wherein the lossy mode resonance layer is a transparent conductive layer.

3. The electrical polarity adjustable biosensor based on lossy mode resonance in claim 1, wherein the bioprobe layer is composed of a metal oxide or a polymer material.

4. The electrical polarity adjustable biosensor based on lossy mode resonance in claim 1, wherein the optical waveguide layer is one of a glass substrate, a quartz substrate, a photonic crystal substrate, and a polymer material substrate.

5. The electrical polarity adjustable biosensor based on lossy mode resonance in claim 1, wherein the plurality of bioprobes are composed of a boride functional group or a DNA probe.

6. An electrical polarity adjustable biosensing system based on lossy mode resonance comprising:
    a broadband light source,
    an input optical fiber coupled to the broadband light source,
    a sensing module coupled to the input optical fiber, and the sensing module including:
    a first polarity module including an optical waveguide layer, a lossy mode resonance layer and a bioprobe layer stacked on each other, the lossy mode resonance layer disposed on one side of the optical waveguide layer, and two opposite sides of the optical waveguide layer being a light input end and a light output end, the bioprobe layer having a plurality of bioprobes, one plane of the bioprobe layer disposed on the lossy mode resonance layer,
    a second polarity module disposed opposite to the first polarity module, the second polarity module including a substrate and a second electrode layer stacked on each other, the second electrode layer adjacent to but not in contact with the bioprobe layer, and
    a plurality of spacers disposed between the first polarity module and the second polarity module, the plurality of spacers simultaneously contacts with the other plane of the bioprobe layer and the second electrode layer, and separate the bioprobe layer and the second electrode layer,
    an output optical fiber coupled to the light output end, and
    a spectrometer coupled to the output optical fiber,
    wherein, an incident light emitted by the broadband light source is configured to lossy mode resonance in the sensing module, a biomaterial sensing region is formed between the lossy mode resonance layer and the second electrode layer, and the biomaterial sensing region has the plurality of bioprobes, the plurality of bioprobes are formed by performing a surface modification on the lossy mode resonance layer, and the biomaterial sensing region is for injecting an object to be tested,
    wherein an electric field is formed between the lossy mode resonance layer and the second electrode layer, the electric field acts on at least one of the pluralities of bioprobes and the object to be tested.

7. The electrical polarity adjustable biosensing system based on lossy mode resonance in claim 6, further comprising an optical fiber attenuator and an analysis host coupled to the optical fiber attenuator, wherein the optical fiber attenuator is coupled to the input optical fiber, and the analysis host is coupled to the spectrometer.

8. The electrical polarity adjustable biosensing system based on lossy mode resonance in claim 6, wherein the lossy mode resonance layer is a transparent conductive layer, the plurality of bioprobes are composed of a boride functional group or a DNA probe.

9. A method of using an electrical polarity adjustable biosensor based on lossy mode resonance, comprising following steps of:

placing an object to be tested on a biomaterial sensing region having a plurality of bioprobes, inputting an incident light emitted by a broadband light source to an optical waveguide layer disposed under the plurality of bioprobes, energizing a lossy mode resonance layer and a second electrode layer to generate an electric field that acts on at least one of the pluralities of bioprobes and the object to be tested, and measuring a light outputted from the optical waveguide layer by a spectrometer, wherein the biomaterial sensing region is formed by sandwiching a plurality of spacers between the lossy mode resonance layer and the second electrode layer, and the plurality of bioprobes are formed by performing a surface modification on the lossy mode resonance layer.

10. The method of using the electrical polarity adjustable biosensor based on lossy mode resonance in claim 9, wherein the plurality of bioprobes are composed of a boride functional group or a DNA probe, the lossy mode resonance layer is a transparent conductive layer, and a substrate is stacked on one plane of the second electrode layer away from the plurality of spacers.

* * * * *